United States Patent
Britt et al.

(10) Patent No.: US 9,489,629 B2
(45) Date of Patent: Nov. 8, 2016

(54) TAILORED SUPPORTING EVIDENCE

(71) Applicant: International Business Machines Corporation, Armonk, NY (US)

(72) Inventors: Michael W. Britt, Rochester, MN (US); Adam C. Lange-Pearson, Rochester, MN (US); Thomas P. Pitzen, Rochester, MN (US); Richard J. Stevens, Monkton, VT (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 4 days.

(21) Appl. No.: 14/576,808

(22) Filed: Dec. 19, 2014

(65) Prior Publication Data

US 2016/0180224 A1    Jun. 23, 2016

(51) Int. Cl.
*G06N 5/00* (2006.01)
*G06N 5/04* (2006.01)
*G06N 99/00* (2010.01)

(52) U.S. Cl.
CPC .............. *G06N 5/04* (2013.01); *G06N 99/005* (2013.01)

(58) Field of Classification Search
CPC ....................................................... G06N 5/02
See application file for complete search history.

(56) References Cited

U.S. PATENT DOCUMENTS

| | | | |
|---|---|---|---|
| 2011/0066587 A1* | 3/2011 | Ferrucci | G06N 5/04 706/54 |
| 2013/0132308 A1* | 5/2013 | Boss | G06F 17/30976 706/12 |
| 2014/0272884 A1 | 9/2014 | Allen et al. | |
| 2014/0272909 A1 | 9/2014 | Isensee et al. | |
| 2014/0280087 A1 | 9/2014 | Isensee et al. | |
| 2014/0297571 A1 | 10/2014 | Beamon et al. | |
| 2014/0298199 A1 | 10/2014 | Johnson, Jr. et al. | |
| 2015/0066968 A1* | 3/2015 | Bastide | G06F 17/30386 707/758 |

* cited by examiner

*Primary Examiner* — Stanley K Hill
*Assistant Examiner* — Ola Olude Afolabi
(74) *Attorney, Agent, or Firm* — Patterson + Sheridan, LLP (57) ABSTRACT

Systems, methods, and computer program products to perform an operation comprising receiving a case from a user, determining a level of sophistication of the user, determining a level of sophistication associated with each of a plurality of items of supporting evidence in a corpus of information, selecting a subset of the plurality of items of supporting evidence based on the determined levels of sophistication, and returning the selected subset to the user as part of a response to the case.

20 Claims, 5 Drawing Sheets

TAILORED SUPPORTING EVIDENCE

BACKGROUND

The present invention relates to deep question answering systems, and more specifically, to deep question answering systems which provide tailored supporting evidence.

Deep question answering systems (deep QA systems) leverage corpora of content that range from basic, introductory level material, to scientific and research-oriented material reflecting the highest level of understanding of the subject domain. Given the broad distribution of content sophistication, the deep QA system may return items of supporting evidence which is not useful to an advanced user, while returning supporting evidence that is not easily comprehended by less experienced users. The supporting evidence may include articles, research papers, or other any other content that supports the candidate answer as being a plausible response to the case.

SUMMARY

Embodiments disclosed herein include systems, methods, and computer program products to perform an operation comprising receiving a case from a user, determining a level of sophistication of the user, determining a level of sophistication associated with each of a plurality of items of supporting evidence in a corpus of information, selecting a subset of the plurality of items of supporting evidence based on the determined levels of sophistication, and returning the selected subset to the user as part of a response to the case.

DETAILED DESCRIPTION

Embodiments disclosed herein provide deep question answering systems (deep QA systems) which tailor the supporting evidence returned to a user based on a level of sophistication associated with that user. For example, if the user has a high level of sophistication, the deep QA system may exclude introductory level supporting evidence, while including scholarly articles in the supporting evidence. Conversely, if the user is a novice having a low level of sophistication, the deep QA system may exclude scholarly articles and return introductory level articles as supporting evidence.

During a training phase, a deep QA system ingests a corpus of documents in a given domain. The deep QA system annotates the corpus to build a model of the "knowledge stored therein. After the training phase, the deep QA system can be asked "questions" (such as a recommended treatment for a patient) about the knowledge. Using the generated models, the deep QA system may return a set of responses (or candidate answers) to the questions. The deep QA system may provide both a measure of confidence of each candidate answer as well as supporting evidence for each candidate answer. The supporting evidence may be any document which includes content supporting the candidate answer as a plausible response to the question.

Generally, the deep QA systems disclosed herein may determine a level of sophistication for each document of supporting evidence from the corpus of information used by the deep QA system to determine an answer. The level of sophistication may be based on the terms and/or concepts used in a document. The deep QA systems may determine the user's level of sophistication from a level of sophistication in a user profile, input provided by the user, a role of the user (such as patient or physician), and a default level of sophistication associated with a deployment of the deep QA system (for example, a deployment in a research hospital may have a high level of sophistication versus a deployment in a high school).

Although the medical field is used herein a reference example, embodiments disclosed herein may apply equally to any type of domain. Generally, using the techniques described herein, deep question answering systems may tailor supporting evidence to measures of user sophistication in any domain.

Figure 1:
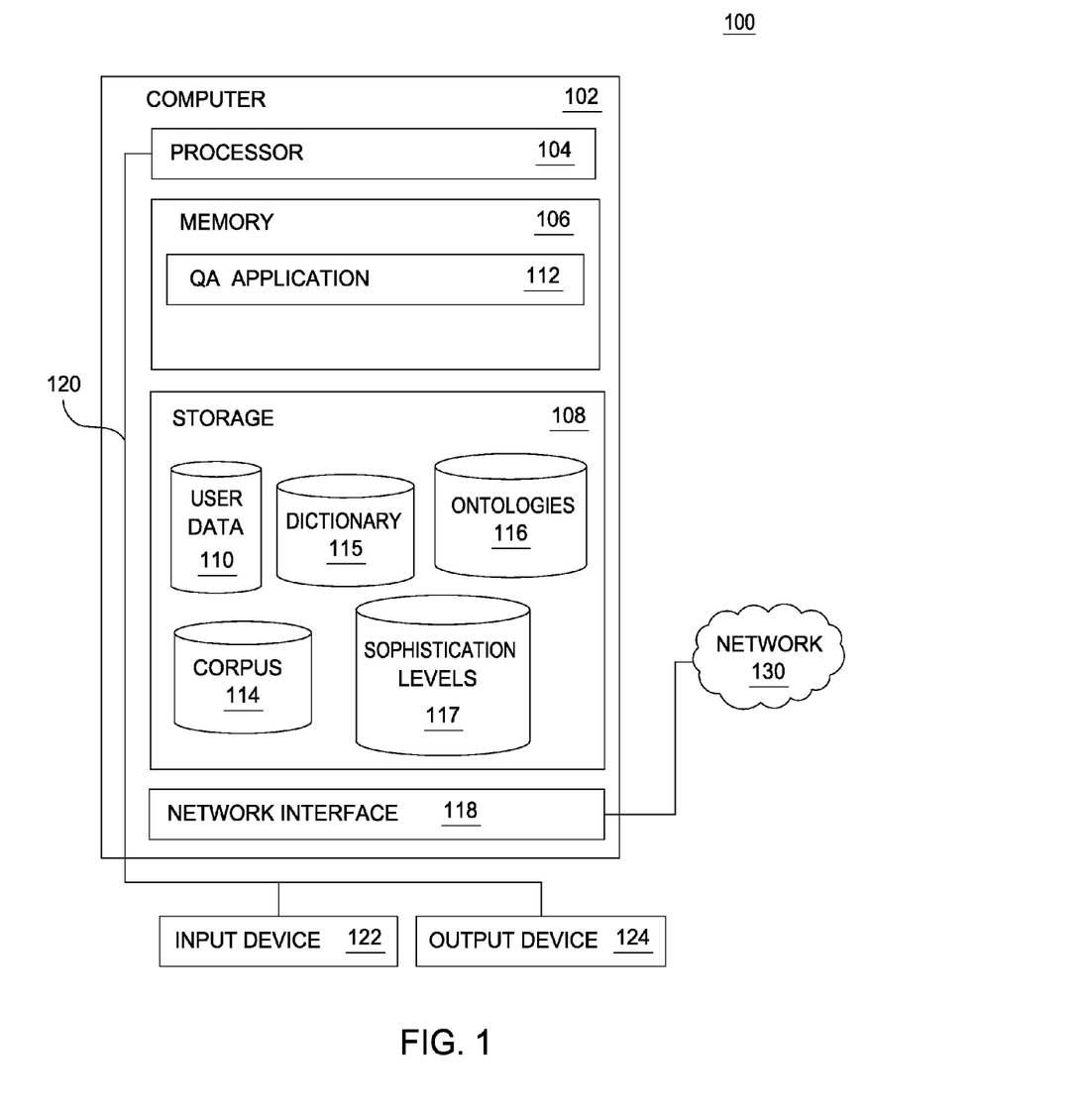
FIG. 1 illustrates a system which provides tailored supporting evidence in a deep question answering system, according to one embodiment.

FIG. 1 illustrates a system 100 which provides tailored supporting evidence in a deep question answering system, according to one embodiment. The networked system 100 includes a computer system 102. The computer system 102 may also be connected to other computers via a network 130. In general, the network 130 may be a telecommunications network and/or a wide area network (WAN). In a particular embodiment, the network 130 is the Internet.

The computer system 102 generally includes a processor 104 which obtains instructions and data via a bus 120 from a memory 106 and/or a storage 108. The computer 102 may also include one or more network interface devices 118, input devices 122, and output devices 124 connected to the bus 120. The computer 102 is generally under the control of an operating system (not shown). Examples of operating systems include the UNIX operating system, versions of the Microsoft Windows operating system, and distributions of the Linux operating system. (UNIX is a registered trademark of The Open Group in the United States and other countries. Microsoft and Windows are trademarks of Microsoft Corporation in the United States, other countries, or both. Linux is a registered trademark of Linus Torvalds in the United States, other countries, or both.) More generally, any operating system supporting the functions disclosed herein may be used. The processor 104 is a programmable logic device that performs instruction, logic, and mathematical processing, and may be representative of one or more CPUs. The network interface device 118 may be any type of network communications device allowing the computer 102 to communicate with other computers via the network 130.

The storage 108 is representative of hard-disk drives, solid state drives, flash memory devices, optical media and the like. Generally, the storage 108 stores application programs and data for use by the computer system 102. In addition, the memory 106 and the storage 108 may be considered to include memory physically located elsewhere; for example, on another computer coupled to the computer system 102 via the bus 120.

The input device 122 may be any device for providing input to the computer 102. For example, a keyboard and/or a mouse may be used. The input device 122 represents a wide variety of input devices, including keyboards, mice, controllers, and so on. The output device 124 may include monitors, touch screen displays, and so on.

As shown, the memory 106 contains a QA application 112, which is generally configured to provide a deep question answering (QA) system. One example of a deep question answering system is Watson, by the IBM Corporation of Armonk, N.Y. A user may submit a case (also referred to as a question) to the QA application 112. The QA application 112 then provides an answer to the case based on an analysis of a corpus of information 114. Although depicted as executing on a single computer, the QA application 112 may run on a grid or cluster of computers (not pictured).

The QA application 112 is trained to generate responses to cases during a training phase. During the training phase, the QA application 112 is trained to answer cases using an "answer key" which predefines the most correct responses. During training, the QA application 112 ingests content in the corpus 114 to produce one or more machine learning models (not pictured). In addition, during the training phase, the QA application 112 is configured to identify data attributes which are important to answering cases (namely, those attributes having an impact on the confidence score of a given answer).

After being trained, the QA application 112 may process user cases through a runtime analysis pipeline. In at least one embodiment, the case data 213 include medical records of a patient, and the candidate answers returned by the QA application 112 correspond to a set of recommended treatments, ranked by a confidence score of each respective candidate answer. The analysis pipeline executes a collection of analysis programs to evaluate both the question text and candidate answers to construct the most probable correct answer, based on the information extracted from the corpus and from the question. A typical execution pipeline may begin with question analysis, which analyzes and annotates each question presented in the case to identify key topics, concepts, and attributes for conducting a search. The next step of the pipeline may include a primary search, which involves searching for documents in the corpus 114 using the key attributes from the question analysis phase. The next step of the pipeline may generate candidate answers. For example, the QA application 112 may identify key matching passages (based on, for example, topics, concepts, and/or string matching) from the search results with passages in the candidate answers. In the next step of the pipeline, the QA application 112 may then retrieve and process supporting evidence for the candidate answers. The QA application 112 may then complete the pipeline by scoring the various candidate answers, from which the most correct answer identified by the QA application 112 may returned to the user along with any retrieved and processed items of supporting evidence.

In one embodiment, the QA application 112 is configured to tailor the supporting evidence returned to the user based on the user's level of sophistication. For example, if the user is a physician at a research hospital, the QA application 112 may return research papers and other scholarly articles related to a specific treatment returned as the best course of treatment for a patient. As another example, if the user is a cancer patient with no medical education or training, the QA application 112 may return articles having a lower level of sophistication, such as techniques to manage pain and other side effects of their treatment. Note, in both cases, the QA application 112 may still evaluate the documents in building an answer in earlier stages of the processing pipeline. For example, the QA application 112 may utilize documents of all levels of sophistication when determining optimal candidate answers to return as responsive to a question (or case). However, the QA application 112 may adjust the evidence returned for display to the user based on the user's level of sophistication and/or role.

To return tailored supporting evidence, the QA application 112 may analyze the content in the corpus 114 to determine a level of sophistication of each item in the corpus 114. Generally, the QA application 112 may use any technique to determine the level of sophistication of content in the corpus 114. For example, the QA application 112 may base the level of sophistication of an article based on one or more of the author, publisher, or other attribute of the article. Additionally, the QA application 112 may reference one or more dictionaries 115 and one or more ontologies 116 to determine the level of sophistication of the content in the corpus 114. For example, the terms and concepts in a given document may be compared with terms in the dictionaries 115 and ontologies 116 to determine a level of sophistication associated with the terms. For example, "skin cancer" may be associated with a lower level of sophistication, while "malignant melanoma" is associated with a higher level of sophistication. Furthermore, the QA application 112 may identify the different sources of information in the corpus 114 that the terms, concepts, and phrases in a given item of content appear. For example, the QA application 112 may compute inverse document frequency (IDF) scores indicating how frequently each term appears in different documents in the corpus 114. For example, the QA application 112 may search the corpus 114, and determine that scholarly articles frequently reference "malignant melanoma," but that patient support forums have frequent references to "skin cancer." As such, the IDF score of "malignant melanoma" may be high in sources in the corpus 114 associated with a high level of sophistication (the scholarly articles), while being lower in sources associated with a lower level of sophistication (the support forums, for example). Likewise, the IDF score for "skin cancer" may be higher in sources in the corpus 114 associated with traditionally lower levels of sophistication (e.g., the user forums). In addition, the IDF score for "skin cancer" in the scholarly articles may be lower than the IDF score for "malignant melanoma." Therefore, the QA application 112 may determine that the user asking about "malignant melanoma" has a higher level of sophistication, while the user asking about "skin cancer" may have a lower level of sophistication.

Based on one or more of the foregoing, the QA application 112 may determine a level of sophistication of each item in the corpus 114. For example, the QA application 112 may assign a high level of sophistication to a scholarly article, and assign a low level of sophistication to a user form post. In one embodiment, the QA application 112 may compute a score for the content. The QA application 112 may compare the computed score to a range sophistication levels 117. The QA application 112 may then assign the sophistication level associated with the computed score to the content. In at least one embodiment, the QA application 112 may store an association of the sophistication level (and/or the computed score) with the item in the corpus 114. Additionally, the QA application 112 may similarly determine levels of sophistication for specific passages or sections of a document in the corpus 114.

The QA application 112 may rely on a variety of available factors to determine a user's level of sophistication. For example, the QA application 112 may reference the user data 110 to identify a level of sophistication in a user profile of the user. In addition, the QA application 112 may analyze inputs provided by the user to refine the user's level of sophistication (such as if the user repeatedly specifies "melanoma" instead of "cancer," and vice versa). Further still, the QA application 112 may determine the user's level of sophistication based on a level of sophistication associated with a deployment of the deep QA system. For example, a high level of sophistication may be the default level of sophistication associated with a deployment of the QA application 112 in a hospital. Further still, the QA application 112 may determine the user's level of sophistication based on the user's role (such as patient, physician, student, and the like). In one embodiment, the QA application 112 may track the user's requests for items of supporting evidence outside of the user's determined level of sophistication. For example, the QA application 112 may present the user with an option to view items of supporting evidence outside of their determined level of sophistication. If a user associated with a low level of sophistication repeatedly requests for items of supporting evidence having a high level of sophistication, the QA application 112 may modify the user's level of sophistication based on the requests for content having a high level of sophistication. As another example, for an unknown user (for whom no sophistication is known), the QA application 112 may monitor what items of supporting evidence the user reviews or accesses, and determine the user's level of sophistication based on the content the user reviews or accesses.

When a user submits a case to the QA application 112, the QA application 112 may match the user's level of sophistication to the levels of sophistication in one or more items of supporting evidence to tailor supporting evidence provided to the user. For example, during supporting evidence processing, the QA application 112 may identify four items of supporting evidence having a high level of sophistication, two items of supporting evidence having a medium level of sophistication, and three items of supporting evidence having a low level of sophistication. If the QA application 112 has determined that the user has a low level of sophistication, the QA application 112 may return the three items of supporting evidence having a low level of sophistication to the user, as the levels of sophistication match. However, the QA application 112 may not present the four items of supporting evidence having the high level of sophistication to the user. In at least one embodiment, however, the QA application 112 may provide the user with an option to view the filtered supporting evidence. In at least one embodiment, the QA application 112 may filter the two items of supporting evidence having the medium level of sophistication, again providing the user the option to view the content on request. However, in at least one embodiment, the QA application 112 may modify the content of the items of supporting evidence to match the user's low level of sophistication. For example, the QA application 112 may change terms or concepts having a medium or high level of sophistication to terms or concepts having a low level of sophistication. For example, the QA application 112 may change "carcinoma" or "malignancy" to "cancer."

In addition, the QA application 112 may be configured to present different passages in a document of supporting evidence to users based on the levels of sophistication of the passages and the users. For example, a first document of supporting evidence may have passages of text having high levels of sophistication, while other passages of the first document of supporting evidence may have low levels of sophistication. Abstracts of full articles are an example of passages that would typically be lower in terms of sophistication, as the abstracts typically provide more of a summary of the information contained within the article. In such a case, the QA application 112 may present a passage having a high level of sophistication (such as a detailed statement within an article) to a first user having a high level of sophistication, while presenting a passage having a low level of sophistication (such as a portion of the abstract) to a second user having a low level of sophistication.

As shown, the storage 108 includes user data 110, a corpus 114, a dictionary 115, ontologies 116, and sophistication levels 117. The user data 110 includes information related to a plurality of different users. The user data 110 may include user profiles that indicate a user's level of sophistication in any number of different areas. For example, one user may be an expert in sociology, but a novice in computer networking. The user profiles in the user data 110 may include any information about the users, including education level, professions, preferred levels of sophistication of supporting evidence, and the like. The corpus 114 is a body of information used by the QA application 112 to generate answers to questions (also referred to as cases). For example, the corpus 114 may contain scholarly articles, dictionary definitions, encyclopedia references, product descriptions, web pages, and the like. The dictionaries 115 may define different terms in one or more disciplines. The ontologies 116 provide a structural framework for organizing information. An ontology formally represents knowledge as a set of concepts within a domain, and the relationships between those concepts.

The sophistication levels 117 may include one or more baseline levels of sophistication, as well as acceptable values for each area of sophistication. The areas of sophistication may correspond to ontology levels, such as a general medical ontology, or different sub-sections of the medical ontology, such as an oncologist or general practitioner sub-section of the ontology. Generally, the representation of a level of sophistication of users or content in the corpus 114 in the sophistication levels 117 (and the user data 110 or the corpus 114) may take any format suitable to represent one or more different levels of sophistication. Furthermore, the QA application 112 may implement any feasible algorithm in order to compute a value for the level of sophistication of users and content in the corpus 114.

Figure 2:
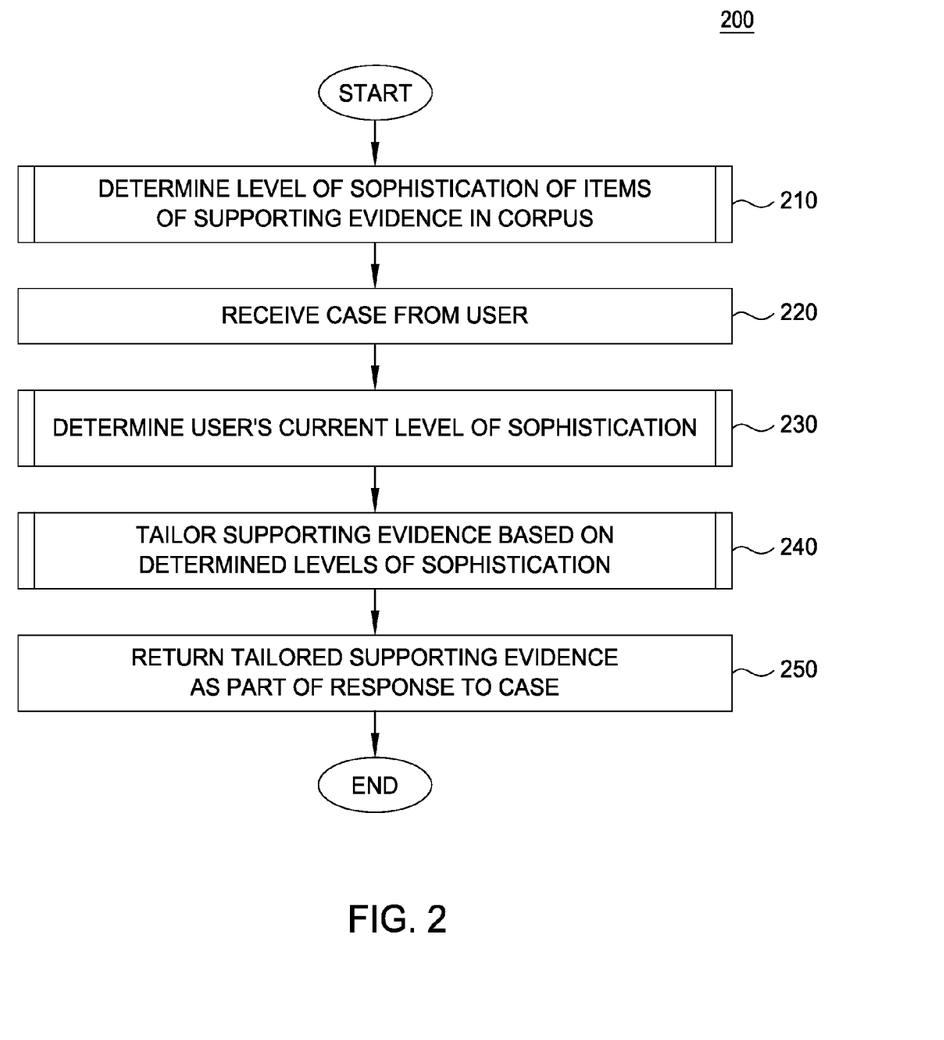
FIG. 2 illustrates a method to provide tailored supporting evidence in a deep question answering system, according to one embodiment.

FIG. 2 illustrates a method 200 to provide tailored supporting evidence in a deep question answering system, according to one embodiment. Generally, the steps of the method 200 provide deep question answering systems that tailor the supporting evidence presented to users based on the levels of sophistication of the supporting evidence and the users. The method 200 begins at step 210, described in greater detail with reference to FIG. 3, where the QA application 112 determines the level of sophistication of each item of supporting evidence in the corpus 114. For example, the QA application 112 may annotate a scholarly article with an indication that the article is of a high level of sophistication. Similarly, the QA application 112 may annotate an article related to home remedies as having a low level of sophistication.

At step 220, the QA application 112 may receive a case (or question) from a user. When the QA application 112 receives the case, the QA application 112 may process the case using a traditional execution pipeline to produce a ranked set of candidate answers and a set of items of supporting evidence for each candidate answer. For example, the QA application 112 may provide three recommended medications as treatment for a patient as candidate answers and supporting evidence in the form scholarly articles for each medication discussing positive results for patients taking the medication. At step 230, described in greater detail with reference to FIG. 4, the QA application 112 may determine the user's current level of sophistication. The QA application 112 may determine the user's level of sophistication based on any number of factors, including without limitation, a level of sophistication stored in the user's profile in the user data 110. At step 240, described in greater detail with reference to FIG. 5, the QA application 112 may tailor the supporting evidence based on the determined levels of sophistication of the user and the supporting evidence. Generally, at step 240, the QA application 112 may filter items of supporting evidence that have levels of sophistication that do not match the user's determined level of sophistication. At step 250, the QA application 112 may return the tailored supporting evidence to the user as part of a response to the case received at step 220.

Figure 3:
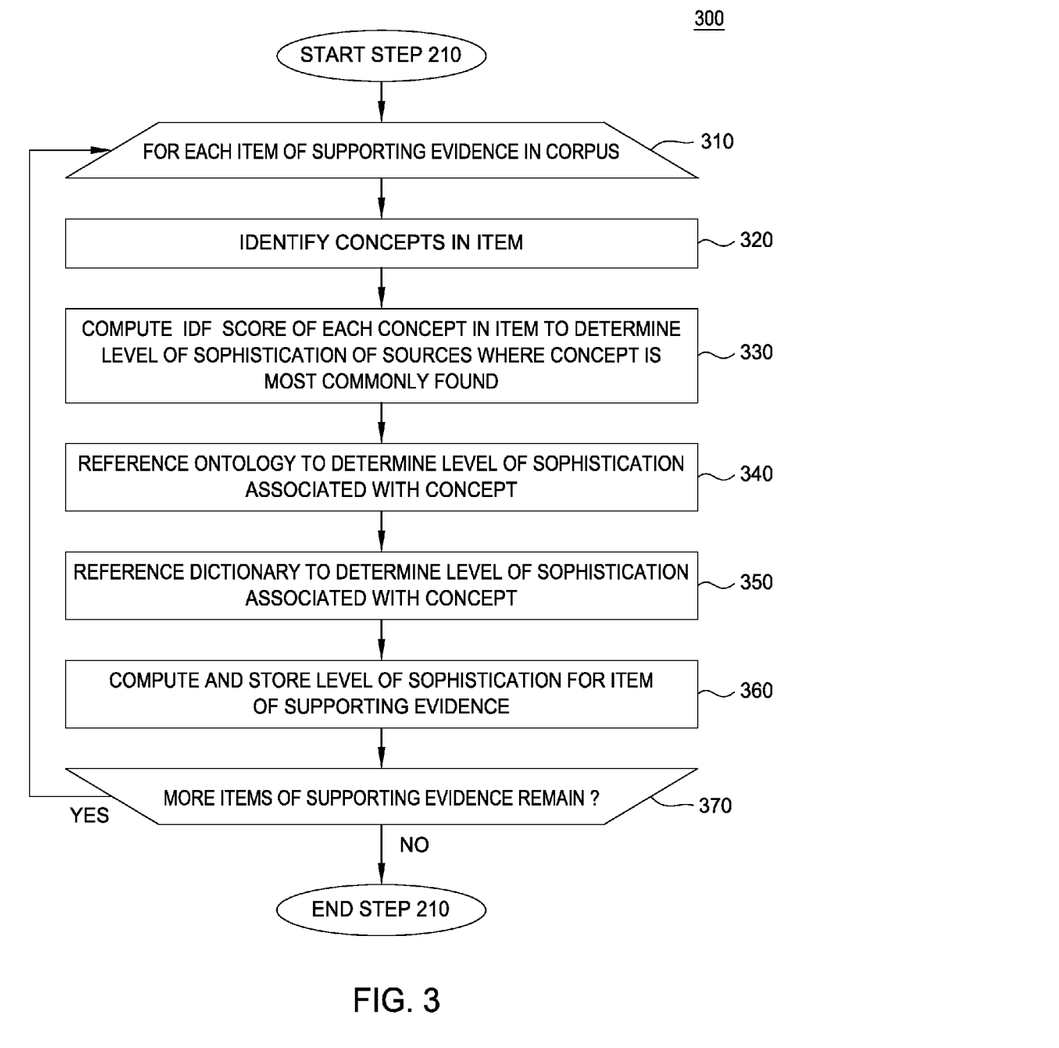
FIG. 3 illustrates a method to determine levels of sophistication of items of supporting evidence in a corpus, according to one embodiment.

FIG. 3 illustrates a method 300 corresponding to step 210, according to one embodiment. That is, FIG. 3 illustrates a method 300 to determine levels of sophistication of items of supporting evidence in a corpus, according to one embodiment. Generally, the QA application 112 may execute the steps of the method 300 to annotate each item of content in the corpus 114 with an associated level of sophistication. The QA application 112 may perform the steps of the method 300 during a training or configuration phase, prior to receiving any questions from users. However, the QA application 112 may periodically execute the steps of the method 300 to maintain current levels of sophistication for the items of supporting evidence in the corpus 114.

The method 300 begins at step 310, where the QA application 112 executes a loop including steps 320-360 for each item of supporting evidence in the corpus 114. The items of supporting evidence may include any type of content, such as research papers, scholarly articles, case studies, web pages, Internet forums, and the like. At step 320, the QA application 112 may identify concepts, topics, (or words) in the item of supporting evidence. At step 330, the QA application 112 may compute an inverse document frequency (IDF) score for each concept to determine where the concepts are most commonly used, and a level of sophistication associated with the sources of information using these concepts most frequently. For example, if a concept in a first article refers to "the little dipper," the QA application 112 may determine that this concept occurs most commonly in web pages created by novice astronomers. As another example, if a concept in a second article refers to "Ursa Minor," the QA application 112 may determine that this concept occurs most commonly in scholarly articles related to astronomy.

At step 340, the QA application 112 may reference the ontologies 116 to determine a level of sophistication associated with each concept in the item of supporting evidence. For example, a term such as "malignant melanoma" may be a specific node in a medical ontology, which may indicate that the term is associated with a higher level of sophistication. However, the term "skin cancer" may be a higher level concept in the ontology, which may reflect a lower level of sophistication. In some embodiments, the QA application 112 may measure sophistication by exploring how many concepts in the ontology are related to the current concepts as child-concepts of the current concepts. If an ontology has many concepts identified as more specific concepts of the current concept, then the QA application 112 may identify the current concept as vague (such as cancer), and give the current concept a lower measure of sophistication. However, if the current concept has very few child-concepts in the ontology, the QA application 112 may consider the current concept to be very specific (such as a malignant melanoma of the left ear lobe), and associate the current concept has having a higher level of sophistication. At step 350, the QA application 112 may reference a dictionary 115 to determine a level of sophistication associated with the identified concepts in the document. For example, if a term is not referenced in a general purpose dictionary, but is referenced in a dictionary associated with a specific scientific discipline, the QA application 112 may determine that the concept is of a higher level of sophistication in the scientific discipline.

At step 360, the QA application 112 may compute a level of sophistication for the item of supporting evidence, and store the computed level of sophistication as an annotation of the item of supporting evidence in the corpus 114. Similarly, the QA application 112 may store the computed level of sophistication in an entry associated with the item of supporting evidence in the sophistication levels 117. In at least one embodiment, the QA application 112 may compute the level of sophistication by computing a score for the item of supporting evidence. Generally, the QA application 112 may compute the score using any algorithm sufficient to produce one or more values that are within a range of acceptable values reflecting different levels of sophistication. For example, the QA application 112 may weigh the heuristics of steps 330-350 to compute a numeric score reflecting the sophistication of the item of supporting evidence. In at least one embodiment, the QA application 112 may then compare this score to the sophistication levels 117 to identify a corresponding level of sophistication. At step 370, the QA application 112 may determine whether more items of supporting evidence remain to be indexed in the corpus 114. If more items of supporting evidence remain, the QA application 112 may return to step 310. If no items of supporting evidence remain to be indexed, the method 300 ends.

Figure 4:
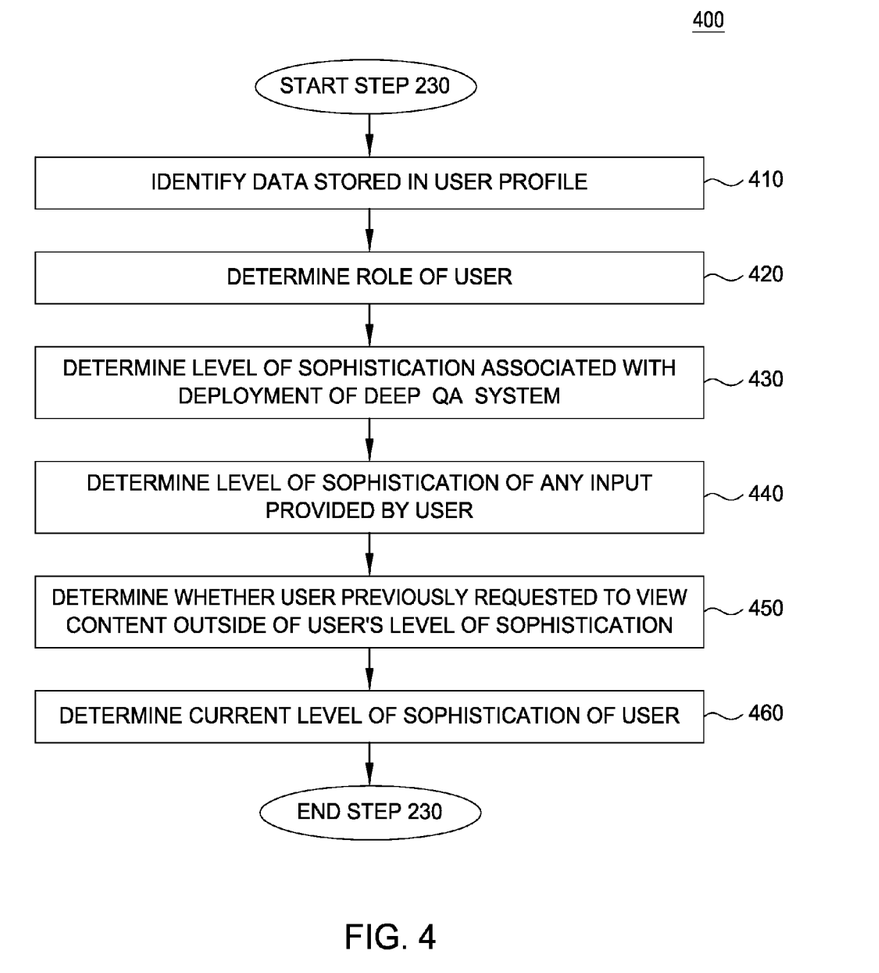
FIG. 4 illustrates a method to determine a current level of sophistication of a user, according to one embodiment.

FIG. 4 illustrates a method 400 to determine a current level of sophistication of a user, according to one embodiment. The method 400 begins at step 410, where the QA application 112 may identify data describing the user stored in a user profile in the user data 110. For example, the user profile may specify a current level of sophistication, education level, profession, specialties, and the like. At step 420, the QA application 112 may determine the user's role (if any), such as patient, physician, caretaker, and the like. In at least one embodiment, the user's role is stored in the user's profile in the user data 110. At step 430, the QA application 112 may determine a default level of sophistication (if any) associated with the deployment of the deep question answering system provided by the QA application 112. For example, if the QA application 112 is deployed in a research hospital, the deployment may be associated with a high level of sophistication. Similarly, if the QA application 112 is deployed in a high school, the deployment may be associated with a medium level of sophistication. The levels of sophistication associated with the deployment of the QA application 112 may be stored in the sophistication levels 117. At step 440, the QA application 112 may determine the level of sophistication of any input provided by the user. For example, if the user types input to the QA application 112 specifying "my belly hurts," the QA application 112 may determine that this input has a low level of sophistication. Similarly, if the user types input specifying "I have an acute pain in my metacarpal," the QA application 112 may determine that the input has a high level of sophistication.

At step 450, the QA application 112 may determine whether the user has previously requested to view content that is outside of the user's level of sophistication. In at least one embodiment, the QA application 112, when presenting a response (including supporting evidence) to a case, may provide users with an option to view supporting evidence at higher or lower levels of sophistication. For example, a user may be determined to have a medium level of sophistication, and the QA application 112 may present the user with supporting evidence having a medium level of sophistication. However, the user may repeatedly request to view supporting evidence having a high level of sophistication. These repeated requests may cause the QA application 112 to provide the supporting evidence having a high level of sophistication by default when processing subsequent cases for the user. At step 460, the QA application 112 may determine the user's current level of sophistication based on one or more of the determinations made at steps 410-450. For example, if a user's profile specifies that the user has a low level of sophistication, but the QA application 112 determines that the user's input is consistently of a high level of sophistication, the QA application 112 may update the user's profile to reflect a medium level of sophistication. Generally, the QA application 112 may use any suitable algorithm to compute the user's level of sophistication. In one embodiment, the QA application 112 computes a score for the user's level of sophistication based on the determinations made at steps 410-450. The QA application 112 may then compare this score to the sophistication levels 117 to identify a corresponding level of sophistication for the user.

Figure 5:
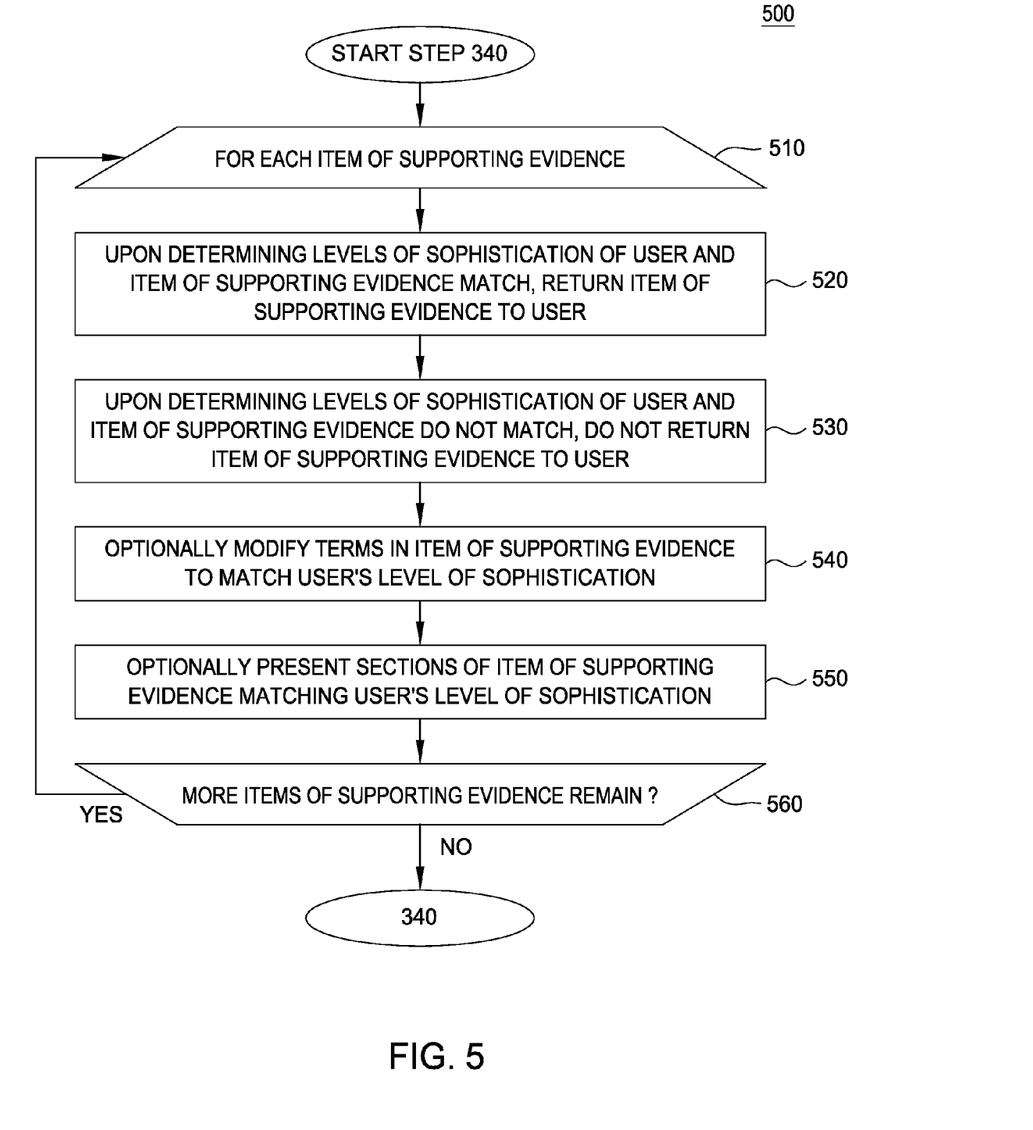
FIG. 5 illustrates a method to tailor supporting evidence, according to one embodiment.

FIG. 5 illustrates a method 500 corresponding to step 240, according to one embodiment. That is, FIG. 5 illustrates a method 500 to tailor supporting evidence, according to one embodiment. The method 500 begins at step 510, where the QA application 112 executes a loop including steps 520-550 for each item of supporting evidence the QA application 112 identifies as supporting one or more candidate answers during the supporting evidence gathering phase of the processing pipeline. At step 520, the QA application 112 may determine that the sophistication levels of the user and the item of supporting evidence match, and return the current item of supporting evidence to the user. Therefore, for example, the QA application 112 may retain (or return to the user) an item of supporting evidence having a high level of sophistication where the user has a high level of sophistication. Similarly, if a sophistication score computed for the user and the item of supporting evidence are within a threshold of each other (or in the same range of sophistication score values), the QA application 112 may return the item of supporting evidence to the user. At step 530, the QA application 112 may filter the current item of supporting evidence upon determining that the levels of sophistication of the item of supporting evidence and the user do not match. Stated differently, the QA application 112 may not present the item of supporting evidence to the user as part of the response to the case. In at least one embodiment, however, the QA application 112 may allow the user to access the filtered item of supporting evidence by providing a link to view filtered supporting evidence.

At step 540, the QA application 112 may optionally modify terms in the item of supporting evidence to match the user's level of sophistication. For example, if an item of supporting evidence has concepts that match the user's level of sophistication, but uses words or phrases that do not match the user's level of sophistication, the QA application 112 may modify the words or phrases to match the user's level of sophistication. Therefore, for example, the QA application 112 may change "carcinoma" to "cancer" where a user does not have a high level of sophistication. At step 550, the QA application 112 may optionally present tailored sections of the item of supporting evidence to the user, where the level of sophistication of the sections match the user's level of sophistication. For example, a first section of a medical study may state that a treatment is contraindicated if the patient has high blood pressure, while stating in a second section that the treatment cannot be given to patients having a high blood pressure. By analyzing the concepts in these two sections (such as by the techniques described in FIG. 3), the QA application 112 may determine that the first section has a high level of sophistication, while the second section has a low level of sophistication. In the event the medical study is returned as an item of supporting evidence, the QA application 112 may present the first section to a first user (having a high level of sophistication), while presenting the second section to a second user (having a low level of sophistication).

At step 560, the QA application 112 may determine whether more items of supporting evidence remain. If more items of supporting evidence remain, the QA application 112 returns to step 510. Otherwise the method 500 ends, and the QA application 112 may return the tailored items of supporting evidence to the user.

Advantageously, embodiments disclosed herein provide deep question answering systems which tailor the supporting evidence returned to users. The tailored supporting evidence is generally of a level of sophistication that matches a level of sophistication of the user. Doing so facilitates the user's understanding of the response generated by the deep question answering system responsive to the case provided by the user.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the foregoing, reference is made to embodiments presented in this disclosure. However, the scope of the present disclosure is not limited to specific described embodiments. Instead, any combination of the recited features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the recited aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

Aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Embodiments of the invention may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g. an amount of storage space consumed by a user or a number of virtualized systems instantiated by the user). A user can access any of the resources that reside in the cloud at any time, and from anywhere across the Internet. In context of the present invention, a user may access applications or related data available in the cloud. For example, the QA application 112 could execute on a computing system in the cloud and provide tailored supporting evidence to users. In such a case, the QA application 112 could determine levels of sophistication of users and items of supporting evidence and store the determined levels of sophistication at a storage location in the cloud. Doing so allows a user to access this information from any computing system attached to a network connected to the cloud (e.g., the Internet).

While the foregoing is directed to embodiments of the present invention, other and further embodiments of the invention may be devised without departing from the basic scope thereof, and the scope thereof is determined by the claims that follow.

What is claimed is:

1. A method, comprising:
   receiving, by a question answering system, a case from a user;
   assigning a first level of user sophistication, of a plurality of levels of user sophistication, to the user;
   determining a level of evidence sophistication, of a plurality of levels of evidence sophistication, associated with each of a plurality of items of supporting evidence in a corpus of information used to process the case;
   selecting, by operation of a computer processor, a subset of the plurality of items of supporting evidence based on the determined levels of user sophistication and evidence sophistication; and
   returning the selected subset to the user as part of a response to the case.

2. The method of claim 1, further comprising:
   assigning a level of evidence sophistication to each item of supporting evidence in the corpus based on at least one of: (i) a concept, subject, or topic of one or more passages in the item of supporting evidence and (ii) unstructured text passages in the item of supporting evidence.

3. The method of claim 1, wherein the first level of user sophistication of the user is assigned based on at least one of: (i) a profile of the user, (ii) a default level of sophistication associated with a deployment of the question answering system, and (iii) a level of sophistication of an input provided by the user.

4. The method of claim 1, wherein the subset includes items of supporting evidence having a determined level of evidence sophistication matching the first level of user sophistication of the user.

5. The method of claim 1, wherein the first level of user sophistication of the user is further assigned based on a role of the user.

6. The method of claim 1, wherein a first item of supporting evidence is not selected as part of the subset, the method further comprising:
   modifying at least one term in the first item of supporting evidence based on the first level of user sophistication of the user; and
   returning the modified first item of supporting evidence to the user as part of the response to the case.

7. The method of claim 1, further comprising:
   receiving a request from the user to view items of supporting evidence having a second level of evidence sophistication, different than the first level of user sophistication of the user; and
   responsive to the request, returning at least one item of supporting evidence having the second level of evidence sophistication to the user.

8. A system, comprising:
   one or more computer processors; and
   a memory containing a program, which when executed by the one or more computer processors, performs an operation comprising:
      receiving, by a question answering system, a case from a user;
      assigning a first level of user sophistication, of a plurality of levels of user sophistication, to the user;
      determining a level of evidence sophistication, of a plurality of levels of evidence sophistication, associated with each of a plurality of items of supporting evidence in a corpus of information used to process the case;
      selecting a subset of the plurality of items of supporting evidence based on the determined levels of user sophistication and evidence sophistication; and
      returning the selected subset to the user as part of a response to the case.

9. The system of claim 8, the operation further comprising:
   assigning a level of evidence sophistication to each item of supporting evidence in the corpus based on at least one of: (i) a concept, subject, or topic of one or more passages in the item of supporting evidence and (ii) unstructured text passages in the item of supporting evidence.

10. The system of claim 8, wherein the first level of user sophistication of the user is assigned based on at least one of: (i) a profile of the user, (ii) a default level of sophistication associated with a deployment of the question answering system, and (iii) a level of sophistication of an input provided by the user.

11. The system of claim 8, wherein the subset includes items of supporting evidence having a determined level of evidence sophistication matching the first level of user sophistication of the user.

12. The system of claim 8, wherein the first level of user sophistication of the user is further assigned based on a role of the user.

13. The system of claim 8, wherein a first item of supporting evidence is not selected as part of the subset, the operation further comprising:
   modifying at least one term in the first item of supporting evidence based on the first level of user sophistication of the user; and
   returning the modified first item of supporting evidence to the user as part of the response to the case.

14. The system of claim 8, the operation further comprising:
- receiving a request from the user to view items of supporting evidence having a second level of evidence sophistication, different than the first level of user sophistication of the user; and
- responsive to the request, returning at least one item of supporting evidence having the second level of evidence sophistication to the user.

15. A computer program product, comprising:
- a non-transitory computer-readable storage medium having computer-readable program code embodied therewith, the computer-readable program code executable by one or more computer processors to perform an operation comprising:
  - receiving, by a question answering system, a case from a user;
  - assigning a first level of user sophistication, of a plurality of levels of user sophistication, to the user;
  - determining a level of evidence sophistication, of a plurality of levels of evidence sophistication, associated with each of a plurality of items of supporting evidence in a corpus of information used to process the case;
  - selecting a subset of the plurality of items of supporting evidence based on the determined levels of user sophistication and evidence sophistication; and
  - returning the selected subset to the user as part of a response to the case.

16. The computer program product of claim 15, wherein the operation further comprises:
- assigning a level of evidence sophistication to each item of supporting evidence in the corpus based on at least one of: (i) a concept, subject, or topic of one or more passages in the item of supporting evidence and (ii) unstructured text passages in the item of supporting evidence.

17. The computer program product of claim 15, wherein the first level of user sophistication of the user is assigned based on at least one of: (i) a profile of the user, (ii) a default level of sophistication associated with a deployment of the question answering system, and (iii) a level of sophistication of an input provided by the user.

18. The computer program product of claim 15, wherein the subset includes a first item of supporting evidence, wherein the level of evidence sophistication of the first item of supporting evidence matches the first level of user sophistication of the user, wherein the subset does not include a second item of supporting evidence, wherein the level of evidence sophistication of the second item of supporting evidence does not first match the level of user sophistication of the user.

19. The computer program product of claim 15, wherein the first level of user sophistication of the user is further assigned based on a role of the user.

20. The computer program product of claim 15, wherein a first item of supporting evidence is not selected as part of the subset, wherein the operation further comprises:
- modifying at least one term in the first item of supporting evidence based on the first level of user sophistication of the user; and
- returning the modified first item of supporting evidence to the user as part of the response to the case.

\* \* \* \* \*